US012270740B2

United States Patent
Kudo

(10) Patent No.: US 12,270,740 B2
(45) Date of Patent: Apr. 8, 2025

(54) ANALYSIS METHOD, ANALYSIS DEVICE AND NON-TRANSITORY COMPUTER READABLE RECORDING MEDIUM STORING PROGRAM

(71) Applicant: SHIMADZU CORPORATION, Kyoto (JP)

(72) Inventor: Yukihiko Kudo, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 273 days.

(21) Appl. No.: 17/421,624

(22) PCT Filed: Feb. 7, 2019

(86) PCT No.: PCT/JP2019/004353
§ 371 (c)(1),
(2) Date: Jul. 8, 2021

(87) PCT Pub. No.: WO2020/161849
PCT Pub. Date: Aug. 13, 2020

(65) Prior Publication Data
US 2022/0074832 A1   Mar. 10, 2022

(51) Int. Cl.
*G01N 1/40* (2006.01)
*G01N 27/62* (2021.01)
*G01N 30/72* (2006.01)

(52) U.S. Cl.
CPC ........... *G01N 1/4044* (2013.01); *G01N 27/62* (2013.01); *G01N 30/7206* (2013.01); *G01N 30/7233* (2013.01)

(58) Field of Classification Search
CPC ........... G01N 30/7206; G01N 30/7233; G01N 1/4044
See application file for complete search history.

(56) References Cited

U.S. PATENT DOCUMENTS

2004/0036018 A1* 2/2004 Deguchi ................. H01J 49/40
                                                    250/281
2010/0285593 A1* 11/2010 Amoura ................. G01N 30/02
                                                    436/174

FOREIGN PATENT DOCUMENTS

JP           2002-267645 A      9/2002

OTHER PUBLICATIONS

Gu et al. "Eliminating Preparation of Multisample External Calibration Curves and Dilution of Study Samples Using the Multiple Isotopologue Reaction Monitoring (MIRM) Technique in Quantitative LC-MS/MS Bioanalysis", Anal. Chem. Jun. 10, 2019, 91, 13, 8652-8659 (Year: 2019).*

(Continued)

*Primary Examiner* — Paul S Hyun
*Assistant Examiner* — Mickey Huang
(74) *Attorney, Agent, or Firm* — Sughrue Mion, PLLC

(57) ABSTRACT

An analysis method is a method of analyzing a second substance in a sample including the second substance produced by decomposition of a first substance, and includes analyzing a sample and a compound having a known concentration and detecting the first substance, the second substance and the above-mentioned compound, calculating an intensity or a concentration of the first substance obtained from the above-mentioned data based on data obtained by the detection and a relative response factor in regard to the first substance and the above-mentioned compound, and producing information about an amount or a concentration of the second substance excluding the second substance produced from the first substance in the analysis, based on an intensity or a concentration of the first substance.

11 Claims, 5 Drawing Sheets

(56) References Cited

OTHER PUBLICATIONS

Gimeno et al., Identification and quantification of 14 phthalates and 5 non-phthalate plasticizers in PVC medical devices by GC-MS, Journal of Chromatography B, vols. 949-950, Feb. 15, 2014, pp. 99-108 (Year: 2014).*
Office Action dated Aug. 2, 2022 issued by the Japanese Patent Office in Japanese Application No. 2020-570282.
International Electrotechnical Commission, "Determination of Certain Substances in Electrotechnical Products—Part 6: Polybrominated biphenyls and polybrominated diphenyl ethers in polymers by gas chromatography-mass spectrometry (GC-MS)," First edition, (the Swiss Confederation), 111/368/FDIS, Jun. 2015, pp. 1-57.
International Search Report of PCT/JP2019/004353 dated May 7, 2019 [PCT/ISA/210].
Written Opinion of PCT/JP2019/004353 dated May 7, 2019 [PCT/ISA/237].
Office Action issued Jun. 27, 2023 in Chinese Application No. 201980090966.X.
Zhen Jiang et al., "Influence of β-arbutin on analysis result of hydroquinone in cosmetics by GC-MS", China Surfactant Detergent & Cosmetics, Feb. 2017, vol. 47, No. 2 (6 pages total).
Communication dated Jan. 4, 2024, issued in Chinese Application No. 201980090966.X.

* cited by examiner

ANALYSIS METHOD, ANALYSIS DEVICE AND NON-TRANSITORY COMPUTER READABLE RECORDING MEDIUM STORING PROGRAM

CROSS REFERENCE TO RELATED APPLICATIONS

This application is a National Stage of International Application No. PCT/JP2019/004353, filed Feb. 7, 2019.

TECHNICAL FIELD

The present invention relates to an analysis method, an analysis device and a non-transitory computer readable recording medium storing a program.

BACKGROUND ART

When a Gas chromatograph/Mass spectrometer (GC/MS) or the like is performed, an introduced substance may be decomposed, and an amount of substance originally included in a sample to be analyzed may not be appropriately measurable. For example, in regard to Decabromodiphenyl ether (Deca-BDE) which is a flame retardant, a reaction product produced by decomposition due to contamination or deterioration of a mass spectrometer is detected in mass spectrometry.

Therefore, before a sample to be analyzed is analyzed, Deca-BDE is introduced into an analysis device, and Deca-BDE and a reaction product are detected. Then, whether the analysis device is in a suitable state for performing an analysis is evaluated (see Non-Patent Document 1).

CITATION LIST

Non Patent Document

[Non-Patent Document 1] International Electrotechnical Commission, "DETERMINATION OF CERTAIN SUBSTANCES IN ELECTROTECHNICAL PRODUCTS—Part 6: Polybrominated biphenyls and polybrominated diphenyl ethers in polymers by gas chromatography-mass spectrometry (GC-MS)," First edition, (the Swiss Confederation), International Electrotechnical Commission, June 2015, p. 22-23

SUMMARY OF INVENTION

Technical Problem

In a case where a substance to be analyzed may be produced by decomposition of another substance in an analysis, it is desirable that the substance to be analyzed is analyzed more efficiently.

Solution to Problem

A first aspect of the present invention relates to an analysis method of analyzing a second substance produced by decomposition of a first substance, that includes analyzing a sample and a compound having a known concentration and detecting the first substance, the second substance and the compound, calculating an intensity or a concentration of the first substance based on data obtained by the detection and a relative response factor in regard to the first substance and the compound, and producing information about an amount or a concentration of the second substance excluding the second substance produced from the first substance in the analysis, based on an intensity or a concentration of the first substance obtained from the data.

A second aspect of the present invention relates to an analysis device that analyzes a second substance produced by decomposition of a first substance, that includes a measurer that detects the first substance, the second substance and a compound by an analysis of a sample and the compound having a known concentration, a calculator that calculates an intensity or a concentration of the first substance based on data obtained by the detection and a relative response factors in regard to the first substance and the compound, and an information producer that produces information about an amount or a concentration of the second substance excluding the second substance produced from the first substance in the analysis based on an intensity or a concentration of the first substance obtained from the data.

A third aspect of the present invention relates to a non-transitory computer readable recording medium storing a program for causing a processing apparatus to execute a process in an analysis of a second substance produced by decomposition of a first substance, wherein the process includes a calculation process of calculating an intensity or a concentration of the first substance based on data obtained by detection of the first substance, the second substance and the compound by an analysis of a sample and a compound having a known concentration, and a relative response factor in regard to the first substance and the compound, and an information production process of producing information about an amount or a concentration of the second substance excluding the second substance produced from the first substance in the analysis based on an intensity or a concentration of the first substance obtained from the data.

Advantageous Effects of Invention

The present invention enables a more efficient analysis of a sample that may include a substance to be analyzed and a substance that produces the substance to be analyzed while suppressing degradation of detection accuracy.

DESCRIPTION OF EMBODIMENTS

Embodiments of the present invention will be described below with reference to the drawings. In the following embodiment, a substance to be analyzed is referred to as a subject substance, and a substance that produces the subject substance by decomposition is referred to as a decomposition parent substance.

First Embodiment

An analysis method of the present embodiment is a method of analyzing a subject substance in a sample that may include the subject substance and a decomposition parent substance, and includes producing information about an amount or a concentration of the subject substance based on a concentration of the detected decomposition parent substance. The information is referred to as analysis information. The concentration of the decomposition parent substance is calculated based on a relative response factor in regard to the decomposition parent substance and a predetermined compound. The predetermined compound is referred to as a reference compound.

(Regarding Sample)

As long as a sample may include a subject sample and a decomposition parent substance, the sample is not limited in particular. As long as a subject substance may be produced from a decomposition parent substance in an analysis, the subject substance or the decomposition parent substance is not limited in particular. The type of decomposition reaction in which a subject substance is produced from a decomposition parent substance is not limited in particular, either. A sample may be any of solid, liquid and gas phases.

A subject substance includes a substance that is industrially manufactured such as an ester of phthalic acid. In the following embodiments, a "phthalate ester" refers to an ester of orthophthalic acid, and "esters of phthalic acid" refer to all of esters of an orthophthalic acid, an isophthalic acid and a terephthalic acid. An ester of phthalic acid, in particular, a phthalate ester, is used industrially as a plasticizer, etc. An ester of phthalic acid, in particular, a phthalate ester tends to be subject to regulation because of negative impact on living organisms, and an efficient quantitative analysis is highly important for quality management or the like of products. Thus, a phthalate ester is preferable as a subject substance.

As one suitable example, a decomposition parent substance is Tris (2-ethylhexyl) trimellitate (TOTM), and a subject substance is at least one compound selected from a group including Di (2-ethylhexyl) phthalate (DEHP), Di (2-ethylhexyl) trephthalate and Di (2-ethylhexyl) isophthalate.

Figure 1:
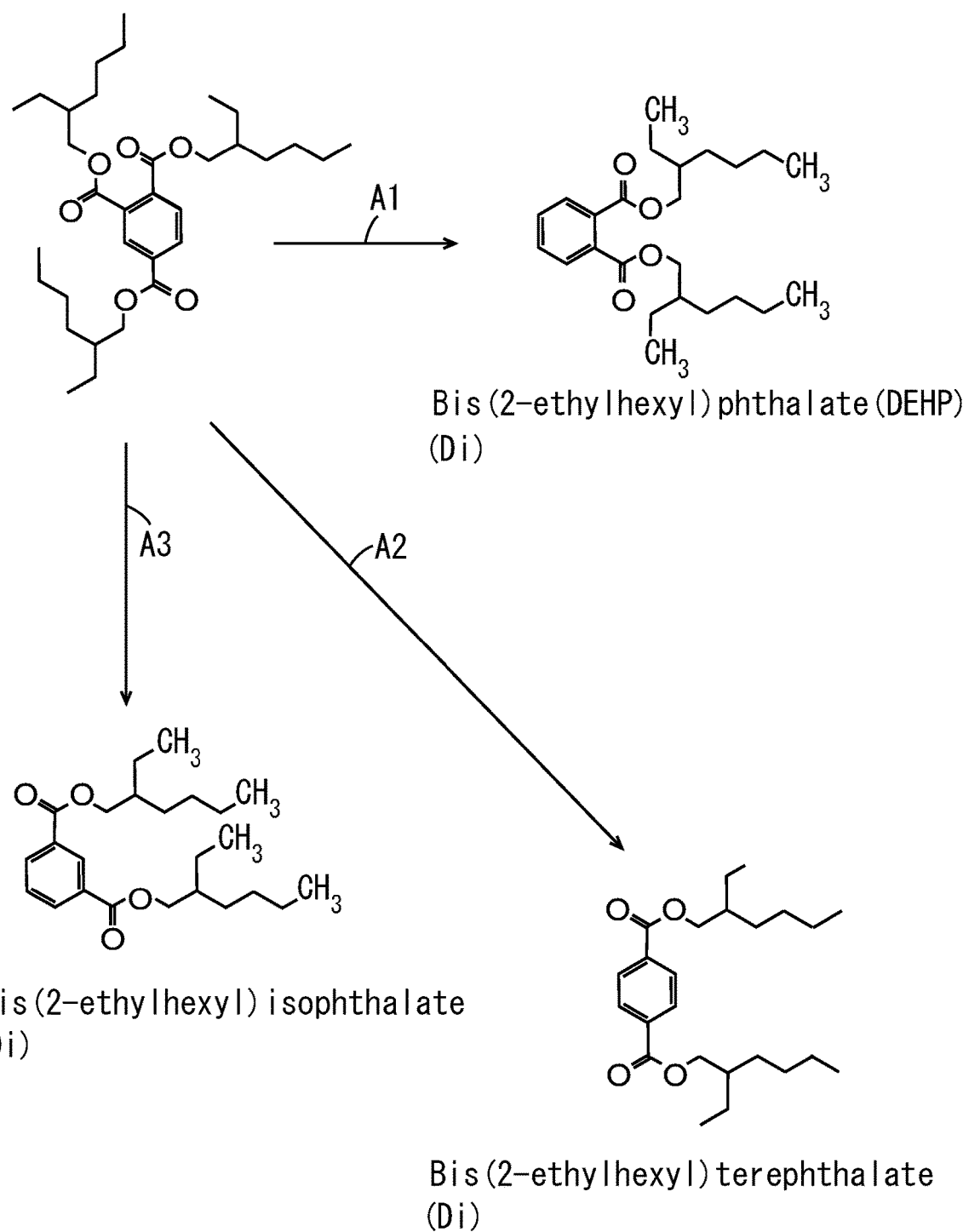
FIG. 1 is a diagram showing Tris (2-ethylhexyl) trimellitate (TOTM) and three compounds produced by its decomposition.

FIG. 1 is a diagram showing the chemical formulas of TOTM and three compounds produced by decomposition of TOTM. Production of DEHP from TOTM is schematically indicated by the arrow A1, production of Di (2-ethylhexyl) trephthalate from TOTM is schematically indicated by the arrow A2, and production of Bis (2-ethylhexyl) isophthalate from TOTM is schematically indicated by the arrow A3.

As another suitable example, a decomposition parent substance is tri trimellitate n-octyl (n-TOTM), and a subject substance is at least one compound selected from a group including Di-n-octyl phthalate (DNOP), Di-n-octyl trephthalate and Di-n-octyl isophthalate.

While being utilized as a plasticizer, DEHP and DNOP are subject to regulation in several countries and regions due to negative impact on living organisms. It is particularly important to efficiently perform a quantitative analysis for quality management of products, etc., and DEHP and DNOP are suitable as subject substances.

In a case where including TOTM or n-TOTM, a sample preferably includes polyvinyl chloride (PVC) as a base resin. It is suggested that TOTM or n-TOTM is likely to decompose when PVC is present, so that the present invention is more suitable in order to enhance accuracy of analysis.

(Regarding Detection)

A sample is subjected to an analysis, and a subject substance, a decomposition parent substance and a reference compound having a known concentration included in the sample are detected. Data obtained by the detection is referred to as measurement data. Intensities of the subject substance, the decomposition parent substance and the reference compound are acquired from the measurement data.

The type of analysis is not limited in particular as long as a quantitative analysis can be performed. For example, at least one of gas chromatography, liquid chromatography, mass spectrometry, Gas Chromatography/Mass Spectrometry (hereinafter referred to as GC/MS), Pyrolysis Gas Chromatography/Mass Spectrometry (hereinafter referred to as Py-GC/MS), Liquid Chromatography/Mass Spectrometry (hereinafter referred to as LC/MS), fourier transform infrared spectroscopy and spectrophotometry utilizing ultraviolet visible light can be used. An analysis of sample is preferably at least one of mass spectrometry, GC/MS, Py-GC/MS and LC/MS. This is because, with mass spectrometry, a relative response factor is particularly stable as described below, and a relative response factor that is obtained in advance can be suitably used.

In a case where a base resin of a sample is PVC, decomposition of TOTM and n-TOTM is observed noticeably in Py-GC/MS. Thus, in a case where a sample includes PVC and at least one of TOTM and n-TOTM, a sample is more preferably analyzed by Py-GC/MS.

(Regarding Reference Compound)

As long as being stable while being analyzed, a reference compound is not limited in particular.

(Regarding Calculation of Concentration)

Concentrations of a subject substance and a decomposition parent substance are calculated from intensities of the subject substance, the decomposition parent substance and a reference compound obtained by an analysis.

While a method of calculating a concentration of a subject substance is not limited in particular, it is preferable from a quantitativity point of view to detect one or more subject substances having known concentrations in advance in the above-mentioned analysis to create a calibration curve, and calculate a concentration of the subject substance from the calibration curve and an intensity of the subject substance obtained in the above-mentioned analysis. However, in a case where quantitativity required for an analysis of a subject substance is not so high, a method of using a relative response factor, described below, may be utilized from an efficiency point of view, or another method may be used.

A concentration of a decomposition parent substance is calculated based on intensities of the decomposition parent substance and a reference compound having a known concentration obtained from measurement data, and a relative response factors (RRF) in regard to the decomposition parent substance and the reference compound. For example, the relative response factor is preferably obtained in advance by an analysis of a decomposition parent substance and a reference compound with the use of an analysis device of the same model as the analysis device used in the above-mentioned analysis. However, as long as an assumed value of the relative response factor is obtained in the above-mentioned analysis, the invention is not limited in particular. Here, a "model" refers to a model of products having measurers having the same specification. It is preferable that a relative response factor in regard to a reference compound and a decomposition parent substance is stored in database or the like in advance for each model or for each device.

A relative response factor is expressed by a ratio of Response Factors (RF) of two substances. Letting a weight of a substance that is subjected to an analysis be M, and letting an intensity obtained by the analysis be A, a response factor RF is expressed by the following formula (1).

$$RF = A/M \qquad (1)$$

A relative response factor of a decomposition parent substance S with respect to a reference compound R is $RRF_{S/R}$. Letting a weight of the reference compound R that is subjected to the analysis be $M_R$, letting an intensity obtained by the analysis be $A_R$, letting a weight of the decomposition parent substance S that is subjected to the analysis be Ms and letting an intensity obtained by the analysis be $A_S$, $RRF_{S/R}$ is expressed by the following formula (2).

$$RRF_{S/R}=(A_S/M_S)/(A_R/M_R) \quad (2)$$

Letting a concentration of the reference compound R used in the analysis for acquisition of $RRF_{S/R}$ be $C_R$, letting a concentration of the decomposition parent substance S be $C_S$, and letting a volume of a sample that is subjected to the analysis be V, $M_R=C_R \times V$ and $M_S=C_S \times V$ hold. From this and the above-mentioned formula (2), $RRF_{S/R}$ is defined by the following formula (3).

$$RRF_{S/R}=(A_S/(C_S \times V))/(A_R/(C_R \times V))=(A_S/C_S)/(A_R/C_R) \quad (3)$$

Therefore, letting a known concentration of the reference compound R used in the past analysis be $C_{R1}$, letting an intensity obtained in the analysis be $A_{R1}$, letting a concentration of the decomposition parent substance S used in the past analysis be $C_{S1}$ and letting an intensity obtained in the analysis be $A_{S1}$, the relative response factor $RRF_{S/R}$ is calculated by the following formula (4).

$$RRF_{S/R}=(A_{S1}/C_{S1})/(A_{R1}/C_{R1}) \quad (4)$$

A relative response factor is kept substantially constant in analysis devices of the same model, in particular, mass spectrometers of the same model. As described above, a value of a relative response factor $RRF_{S/R}$ is obtained in advance with the use of the device of the same model as the analysis device used for an analysis of a sample in the past. Letting a known concentration of the reference compound R be $C_{R2}$, letting an intensity of the reference compound R obtained from measurement data be $A_{R2}$, letting an intensity of the decomposition parent substance S be $A_{S2}$, a concentration $C_{S2}$ of the decomposition parent substance S is expressed by the following formula (5) with the use of the relative response factor $RRF_{S/R}$.

$$C_{S2}=RRF_{S/R} \cdot A_{S2}/(A_{R2}/C_{R2}) \quad (5)$$

In a case where a concentration of the decomposition parent substance is calculated with the use of a relative response factor as described above, it is not necessary to create a calibration curve in regard to the decomposition parent substance in advance, and a work amount for an analysis of a sample can be reduced. As compared to a quantitative analysis of a subject substance, high quantitativity is often not required for a quantitative analysis of a decomposition parent substance. It is suitable to use a relative response factor for calculation of a concentration of the decomposition parent substance in terms of efficiently performing an analysis while suppressing quantitativity of the subject substance.

The concentration of the decomposition parent substance may be calculated based on a relative response factor of a reference compound with respect to the decomposition parent substance.

(Production of Analysis Information)

Analysis information is produced based on calculated concentrations of a subject substance and a decomposition parent substance. Analysis information is information about an amount or concentration of a subject substance in a sample and can include information about reliability of the amount or the concentration in the analysis. Analysis information is provided to an analyst or the like.

While analysis information is produced based on a threshold value (hereinafter referred to as a first threshold value) in regard to a concentration of a decomposition parent substance and a threshold value (hereinafter referred to as a second threshold value) in regard to a concentration of a subject substance in the following description, by way of example, a method of producing the analysis information is not limited in particular as long as information about an amount or a concentration of the subject substance is obtained based on the concentration of the decomposition parent substance. Here, a second threshold value is a value suitably defined in accordance with the purpose or the like of an analysis. For example, in a case where a subject substance is subject to regulation, a second threshold value is set based on a concentration allowed by the regulation.

Figure 2A:
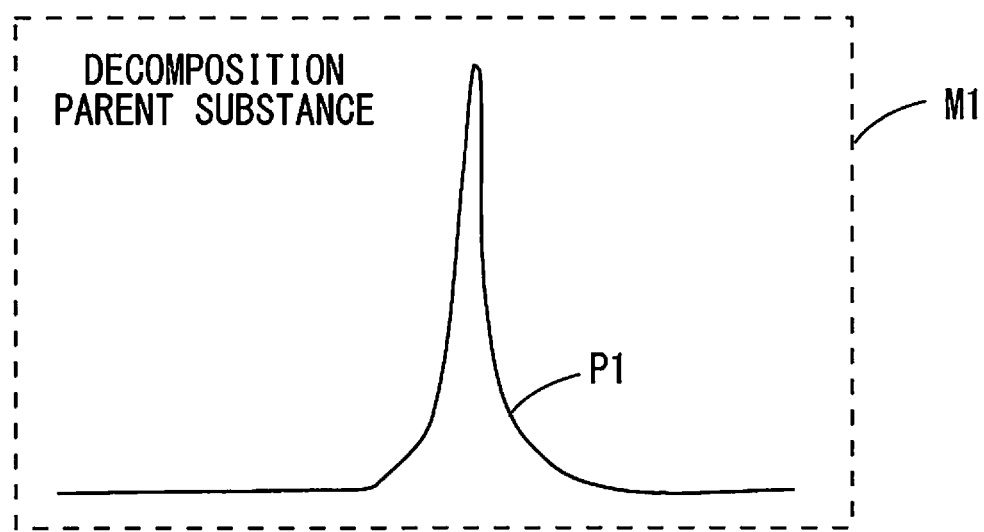
FIG. 2A is a mass chromatogram showing a peak corresponding to TOTM.
Figure 2B:
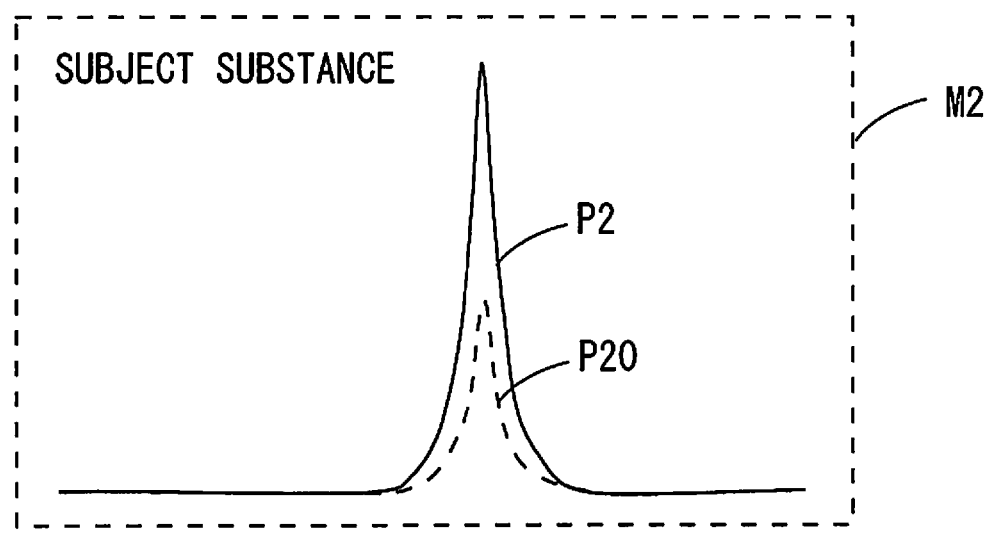
FIG. 2B is a conceptual diagram showing a peak corresponding to Bis (2-ethylhexyl) phthalate (DEHP).

FIGS. 2A and 2B are conceptual diagrams for explaining production of analysis information. FIG. 2A is a mass chromatogram M1 including a peak (hereinafter referred to as a first peak P1) corresponding to a decomposition parent substance. FIG. 2B is a mass chromatogram M2 including a peak (hereinafter referred to as a second peak P2) corresponding to a subject substance. In FIGS. 2A and 2B, the abscissa indicates a retention time, and the ordinate indicates an intensity of a detection signal.

In a case where an intensity of the first peak P1 corresponding to the decomposition parent substance is equal to or larger than a certain value, it is determined that the decomposition parent substance is included in a sample to the extent that decomposition of the decomposition parent substance being analyzed affects an analysis of the subject substance. In this case, out of the subject substance corresponding to the second peak P2, a portion that is based on the decomposition parent substance is a subject substance produced by decomposition of the decomposition parent substance in the analysis. Therefore, a peak P20 corresponding to the subject substance included in the sample before the analysis is presumed to be smaller than the second peak P2.

In consideration of the above, whether the calculated concentration of the decomposition parent substance is equal to or larger than the first threshold value is determined (hereinafter referred to as a first determination). In a case where the concentration of the decomposition parent substance is equal to or larger than the first threshold value, correction is made such that the calculated concentration of the subject substance is lower, or correction is made such that the second threshold value is higher. After the correction, whether the concentration of the subject substance is equal to or larger than the second threshold value is determined (hereinafter referred to as a second determination). In a case where the concentration of the decomposition parent substance is smaller than the first threshold value, the second determination is made without the correction. A change amount in the correction of the concentration of the subject substance or the second threshold value, and the first threshold value are defined based on the preobtained information about how much subject substance is produced from the decomposition parent substance in the analysis. Detection of the decomposition parent substance may be a condition for the first determination. In other words, the first threshold value may be 0 or a value defined based on noise of a detection signal in a case where ions are not detected.

A determination condition in regard to each of the first threshold value and the second threshold value is not limited in particular as long as a determination is made based on the first threshold value or the second threshold value. For example, a determination may be made not based on whether the concentration is the above-mentioned "equal to or larger than the first threshold value" but based on whether the concentration exceeds the first threshold value, for example.

Analysis information including a result of the second determination is provided to the analyst or the like. Further, the analysis information may include a result of the first determination or information relating to whether the above-mentioned correction is made.

In a case where the concentration of the decomposition parent substance is equal to or larger than the first threshold value in the first determination, the second determination may be made without the above-mentioned correction, and analysis information including a result of the second determination and information about degradation of reliability of the second determination due to the effect of the decomposition parent substance may be provided.

(Regarding Analysis Device)

Figure 3:
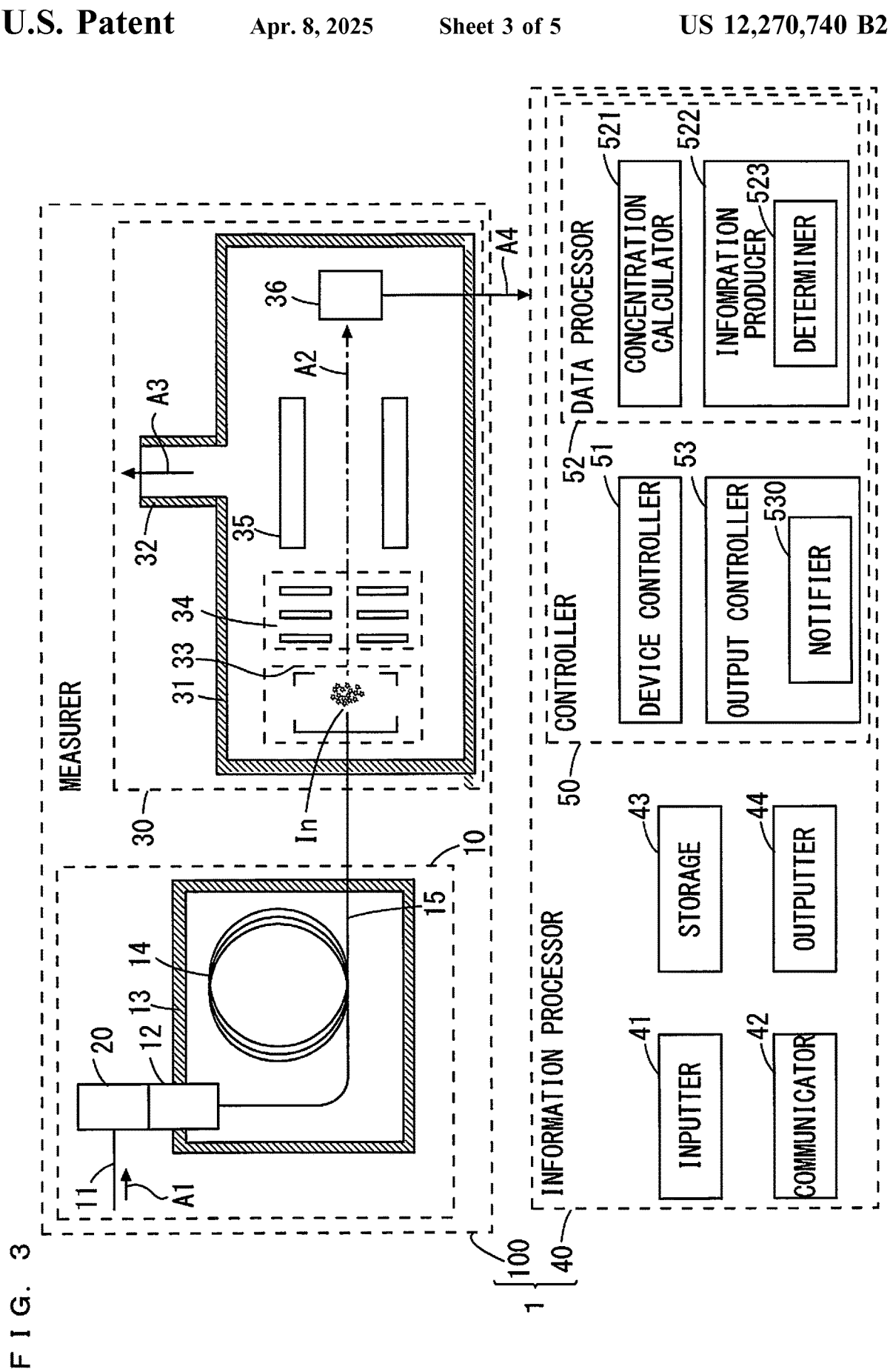
FIG. 3 is a conceptual diagram showing the configuration of an analysis device according to one embodiment.

FIG. 3 is a conceptual diagram showing the configuration of the analysis device according to the present embodiment. The analysis device 1 includes a Pyrolysis Gas Chromatograph-Mass Spectrometer (hereinafter referred to as a Py-GC-MC) and includes a measurer 100 and an information processor 40. The measurer 100 includes a pyrolysis gas chromatograph 10 and a mass spectrometry unit 30.

As long as being able to perform a quantitative analysis, the analysis device according to the present embodiment is not limited in particular. As the analysis device, a Gas Chromatograph (GC), a Liquid Chromatograph (LC), a mass spectrometer, a Gas Chromatograph-Mass Spectrometer (GC-MS), a Liquid Chromatograph-Mass Spectrometer (LC-MS), a fourier transform infrared spectrometer, a UV-visible spectrophotometer or the like can be used.

The pyrolysis gas chromatograph 10 includes a pyrolysis apparatus 20, a carrier gas flow path 11, a sample introducer 12 into which a sample that is pyrolytically decomposed in the pyrolysis apparatus 20 and a reference compound (hereinafter referred to as a "sample or the like") are introduced, a column temperature adjuster 13, a separation column 14 and a sample gas introduction tube 15. The mass spectrometry unit 30 includes a vacuum container 31, an exhaust port 32, an ionizer 33 that ionizes a sample or the like and produces ions In, an ion adjuster 34, a mass separator 35 and a detector 36.

The information processor 40 includes an inputter 41, a communicator 42, a storage 43, an outputter 44 and a controller 50. The controller 50 includes a device controller 51, a data processor 52 and an output controller 53. The data processor 52 includes a concentration calculator 521 and an information producer 522. The output controller 53 includes a notifier 530. The information producer 522 includes a determiner 523.

The measurer 100 separates a sample or the like into components by a separation analysis and detects the sample or the like.

The pyrolysis gas chromatograph 10 pyrolitically decompose a sample or the like and then obtains components included in the sample or the like by separation based on physical properties or chemical properties. A sample or the like is gas or gaseous when being introduced into the separation column 14 and is referred to as a sample gas.

The carrier gas flow path 11 is a flow path for a carrier gas such as helium and introduces the carrier gas into the pyrolysis apparatus 20 (the arrow A1). The pyrolysis apparatus 20 pyrolytically decompose a sample or the like and introduces the sample or the like into the sample introducer 12. The type of the pyrolysis apparatus 20 is not limited in particular, and may be a furnace type, an induction heating type or a filament type. The sample introducer 12 includes a chamber into which a sample or the like is introduced, a split vent, etc. and introduces a sample gas suitably and selectively into the separation column 14.

The separation column 14 includes a column such as a capillary column. The temperature of the separation column 14 is controlled at several hundred ° C. or less by the column temperature adjuster 13 including a column oven or the like. A sample gas is separated into components based on a distribution coefficient between a mobile phase and a stationary phase of the separation column 14, etc., and components into which the sample gas is separated are respectively eluted from the separation column 14 at different times and introduced into the ionizer 33 of the mass spectrometry unit 30 through the sample gas introduction tube 15.

The mass spectrometry unit 30 includes a mass spectrometer, ionizes a sample or the like that has been introduced into the ionizer 33 and detects ions by mass separation. A path through which ions In produced by the ionizer 33 flow is schematically indicated by the arrow A2. Ions In include ions in which electrons, atoms or atom groups are combined with a sample or the like, ions derived from the sample or the like such as ions produced by decomposition such as dissociation, etc. of the sample or the like.

As long as being able to detect ions In with desired accuracy by mass spectrometry, the type of a mass spectrometer that constitutes the mass spectrometry unit 30 is not limited in particular. A mass spectrometer that includes one or more mass spectrometry devices of any type may be used.

The vacuum container 31 of the mass spectrometry unit 30 includes the exhaust port 32. The exhaust port 32 is connected to a vacuum exhaust system (not shown) that includes a pump such as a turbo-molecular pump that can realize a high vacuum state such as $10^{-2}$ Pa or less and its auxiliary pump. In FIG. 3, exhaust of gas in the vacuum container 31 is indicated schematically by the arrow A3.

The ionizer 33 of the mass spectrometry unit 30 includes an ion source and ionizes a sample or the like introduced into the ionizer 33 by electronic ionization. Because a sample or the like is dissociated when being electronically ionized, ions In include fragment ions obtained by dissociation of the sample or the like. Ions In produced by the ionizer 33 are introduced into the ion adjuster 34.

An ionization method performed by the ionizer 33 is not limited in particular as long as ionization can be performed with desired efficiency. In case of GC-MS, chemical ionization or the like may be used. In case of LCMS, an electrospray method or the like can be suitably used.

The ion adjuster 34 of the mass spectrometry unit 30 includes an ion transport system such as a lens electrode or an ion guide and makes adjustment by focusing ions In using electromagnetic action, etc. Ions In emitted from the ion adjuster 34 are introduced into the mass separator 35.

The mass separator 35 of the mass spectrometry unit 30 includes a quadrupole mass filter and performs mass separation of introduced ions In. The mass separator 35 causes ions In to pass selectively based on an m/z value by a voltage applied to the quadrupole mass filter. Ions In obtained by mass separation in the mass separator 35 enter the detector 36.

The detector 36 of the mass spectrometry unit 30 includes an ion detector and detects entered ions In. The detector 36 converts a detection signal obtained by detection of entered ions In into a digital signal by an A/D converter (not shown) and outputs the digitalized detection signal to the information processor 40 as measurement data (the arrow A4).

The information processor 40 includes an information processing apparatus such as an electronic calculator and executes processes such as communication, storage, calculation, etc. in regard to various data in addition to serving as an interface with respect to a user of the analysis device 1 (hereinafter simply referred to as a "user.")

Further, part of data used by the analysis device 1 may be saved in a remote server or the like, and part of a calculation process executed by the analysis device 1 may be executed by the remote server or the like.

The inputter 41 is constituted by an input device such as a mouse, a keyboard, various buttons or a touch panel. The inputter 41 receives information and so on required for control of the measurer 100 or a process executed by the controller 50 from the user. An m/z for detection of ions In is input via the inputter 41. The communicator 42 is constituted by a communication device that can communicate via wireless connection or wired communication such as the Internet, and suitably transmits and receives data and so on in regard to the control of the measurer 100 or a process executed by the controller 50.

The storage 43 is constituted by a non-volatile storage medium and stores measurement data, a program for execution of a process by the controller 50, data required for execution of a process by the data processor 52, data obtained by the process, etc. In the storage 43, numerical values representing a first threshold value, a second threshold value and a relative response factor $RRF_{S/R}$, described above, and data for correction of a concentration of a subject substance or a second threshold value is stored.

The outputter 44 is constituted by a display device such as a liquid crystal monitor, a printer or the like. The outputter 44 outputs data or the like obtained by a process executed by the data processor 52 by displaying the data or the like in the display device or printing the data or the like using a printer.

The controller 50 includes a processor such as a CPU, and serves as a main constituent of behavior of the analysis device 1 by controlling the operation of each component of the measurer 100, processing measurement data, etc.

The device controller 51 of the controller 50 controls the operation of each component of the measurer 100. For example, the device controller 51 can detect ions In in a scan mode in which an m/z of ions passing through the mass separator 35 changes continuously or an SIM (Selective Ion Scanning) mode in which a plurality of ions having a specific m/z pass. In this case, the device controller 51 changes a voltage of the mass separator 35 such that ions In having an m/z that is set based on input from the inputter 41, or the like selectively pass through the mass separator 35.

The data processor 52 of the controller 50 processes and examines measurement data.

The concentration calculator 521 calculates intensities of a detected subject substance and a detected decomposition parent substance from the measurement data. The concentration calculator 521 produces data corresponding to a mass chromatogram (hereinafter referred to as mass chromatogram data) from the measurement data. The concentration calculator 521 calculates peak intensities or peak areas of peaks respectively corresponding to a subject substance, a decomposition parent substance and a reference compound as intensities of the subject substance, the decomposition parent substance and the reference compound.

A method of calculating intensities of a subject substance, a decomposition parent substance and a reference compound is not limited in particular as long as a quantitative analysis of levels of detection signals corresponding to these substances or compounds can be performed from measurement data.

The concentration calculator 521 calculates a concentration of a subject substance based on a calculated intensity of the subject substance. While it is preferable that a concentration of a subject substance is calculated based on a calibration curve, the invention is not limited to this. The concentration calculator 521 calculates a concentration of a decomposition parent substance by the above-mentioned formula (5) based on intensities of the decomposition parent substance and a reference compound, and a relative response factor in regard to the decomposition parent substance and the reference compound stored in the storage 43.

The information producer 522 produces analysis information. An amount or a concentration of a subject substance included in analysis information is an amount or a concentration of the subject substance excluding a subject substance produced from a decomposition parent substance in an analysis performed by the analysis device 1.

The determiner 523 of the information producer 522 makes a first determination in regard to a concentration of a decomposition parent substance calculated by the concentration calculator 521. In a case where a concentration of a decomposition parent substance is equal to or larger than a first threshold value, the determiner 523 makes reference to data for correction of a concentration of a subject substance or a second threshold value (hereinafter referred to as correction data) stored in the storage 43. In correction data, a correction amount of a concentration of a subject substance or a second threshold value is set in correspondence with a concentration of a decomposition parent substance. The determiner 523 corrects a concentration of a subject substance or a second threshold value based on correction data. After the correction, or in a case where a concentration of a decomposition parent substance is smaller than a first threshold value in the first determination, the determiner 523 makes a second determination.

The information producer 522 creates analysis information including a result of determination of the second determination. The analysis information suitably includes information about reliability of the first determination, the above-mentioned correction and the second determination.

The output controller 53 produces an output image including analysis information or the like obtained by a process executed by the data processor 52, and controls the outputter 44 and causes the outputter 44 to output the output image.

The notifier 530 of the output controller 53 outputs a notification for notifying the user of at least part of the analysis information. While a notification method performed by the notifier 530 is not limited in particular, a notification may be displayed as a pop-up message in a screen of the outputter 44, for example. For example, in a case where it is determined in a first determination that a concentration of a decomposition parent substance is equal to or larger than a first threshold value, the user can be notified that a concentration of a subject substance may be presented as being higher than a concentration before an analysis due to the effect of the decomposition parent substance. Alternatively, in a case where a concentration of a subject substance or a second threshold value is corrected after a first determination made by the determiner 523, the notifier 530 can provide a notification representing that the correction is performed.

(Regarding Analysis Method)

Figure 4:
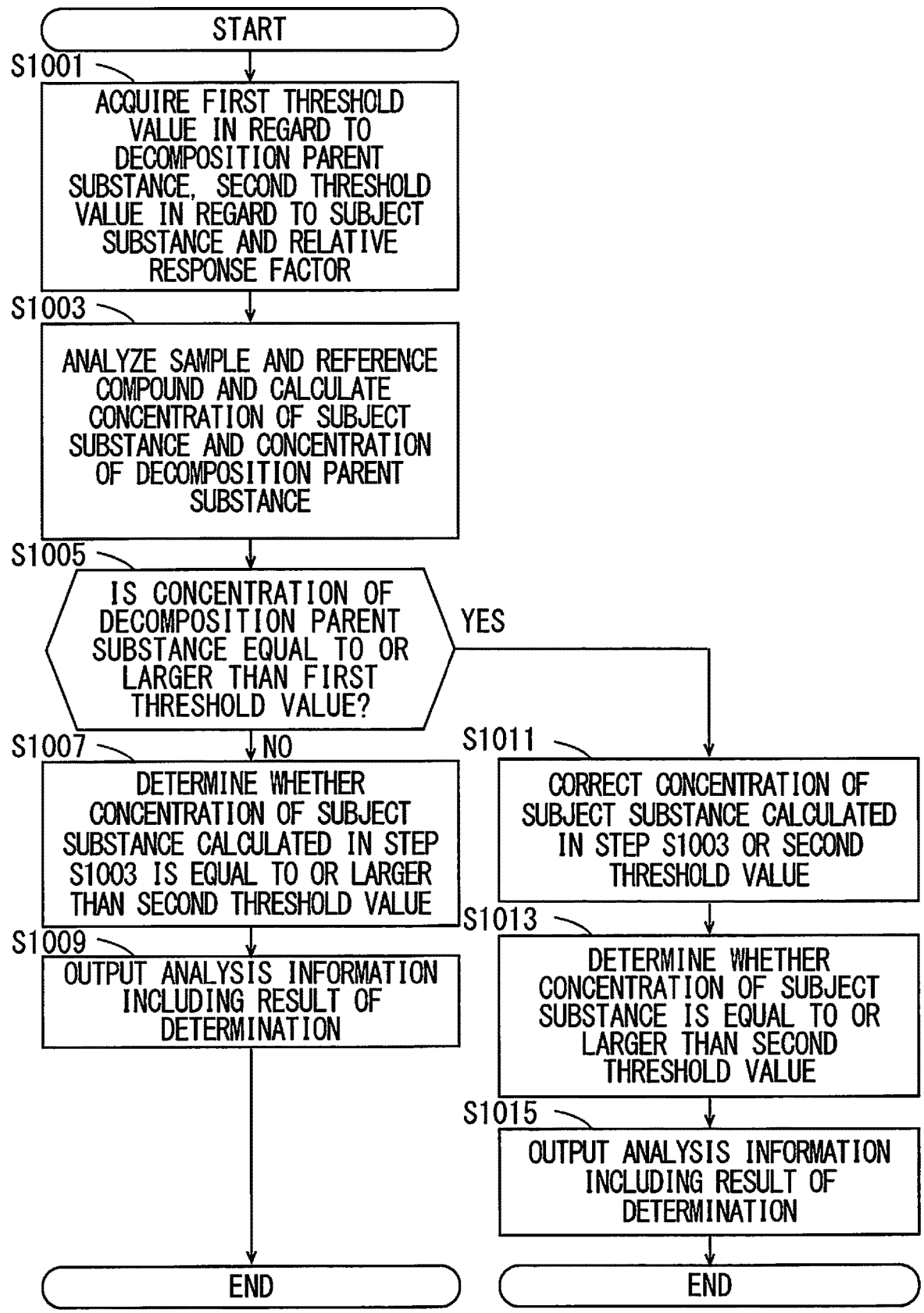
FIG. 4 is a flowchart showing a flow of an analysis method according to the one embodiment.

FIG. 4 is a flowchart showing a flow of the analysis method of the present embodiment. In the step S1001, the information processor 40 acquires a first threshold value, a second threshold value and a relative response factor in regard to a decomposition parent substance and a reference compound and causes the storage 43 to store them. When the step S1001 ends, the step S1003 is started. In the step S1003, the measurer 100 analyzes a sample and the reference compound, and the concentration calculator 521 calculates a concentration of the subject substance and a concentration of the decomposition parent substance. When the step S1003 ends, the step S1005 is started.

In the step S1005, the determiner 523 determines whether the concentration of the decomposition parent substance is equal to or larger than a first threshold value (the first determination). In a case where the concentration of the decomposition parent substance is smaller than the first threshold value, the determiner 523 makes negative determination in regard to the step S1005, and the step S1007 is started. In a case where the concentration of the decomposition parent substance is equal to or larger than the first threshold value, the determiner 523 makes affirmative determination in regard to the step S1005, and the step S1011 is started.

In the step S1007, the determiner 523 determines whether the concentration of the subject substance calculated in the step S1003 is equal to or larger than a second threshold value (the second determination). When the step S1007 ends, the step S1009 is started. In the step S1009, the outputter 44 outputs analysis information including a result of determination of the second determination.

In the step S1011, the determiner 523 corrects the concentration of the subject substance calculated in the step S1003 or the second threshold value. When the step S1011 ends, the step S1013 is started. In the step S1013, the determiner 523 determines whether the concentration of the subject substance is equal to or larger than the second threshold value (the second determination). When the step S1013 ends, the step S1015 is started.

In the step S1015, the determiner 523 outputs analysis information including a result of determination of the second determination. When the step S1015 ends, the process ends.

Following modifications is in the scope of the present invention and can be combined with the above-mentioned embodiment. In the below-mentioned modified example, parts having structure and functions similar to those of the above-mentioned embodiment are denoted with the same reference numerals, and a description will suitably be not repeated.

Modified Example 1

In the above-mentioned embodiment, in a first determination, in a case where a concentration of a decomposition parent substance is equal to or larger than a first threshold value, a concentration of a subject substance or a second threshold value is corrected. However, the first threshold value may be set as an intensity value, and the first determination may be made based on whether an intensity of the decomposition parent substance obtained from measurement data is equal to or larger than the first threshold value. In this case, although the concentration of the decomposition parent substance is not required in the first determination, the outputter 44 can output the concentration of the decomposition parent substance calculated with the use of a relative response factor as described above, and the concentration can be provided to an analyst or the like.

Modified Example 2

In the above-mentioned embodiment, in a case where a decomposition parent substance includes at least one of TOTM and n-TOTM, whether a first determination is to be made based on whether PVC or a compound derived from PVC (hereinafter referred to as PVC or the like) is detected in an analysis of a sample may be determined. In a case where PVC or the like is detected, a subject substance is more likely to be produced from TOTM or n-TOTM in an analysis. Therefore, it is possible to perform a quantitative analysis of a subject substance more efficiently by making the first determination in a case where PVC or the like is detected. In this manner, the information producer 522 can produce analysis information based on whether PVC is detected in an analysis of a sample.

Modified Example 3

A program for implementing an information processing function of the analysis device 1 may be recorded in a computer-readable recording medium. A computer system may read the program, which is recorded in the recording medium, in regard to the control of a process to be executed by the above-mentioned data processor 52 and its related processes and execute the program. A "computer system" here includes hardware such as an OS (Operating System) or peripheral appliances. Further, a "computer-readable recording medium" refers to a movable recording medium such as a flexible disc, an optical magnetic disc, an optical disc or a memory card and a storage device such as a hard disc built into the computer system. Further, a "computer-readable recording medium" may include an object that retains a program movably for a short period of time such as a communication wire that is used when a program is transmitted through a network such as the Internet or a communication line such as a telephone line, or an object that retains a program for a certain period of time such as a volatile memory in a computer system that serves as a server or a client. Further, the above-mentioned program may be to implement part of the above-mentioned functions and may further be to implement the above-mentioned functions by being combined with a program that has already been recorded in the computer system.

Figure 5:
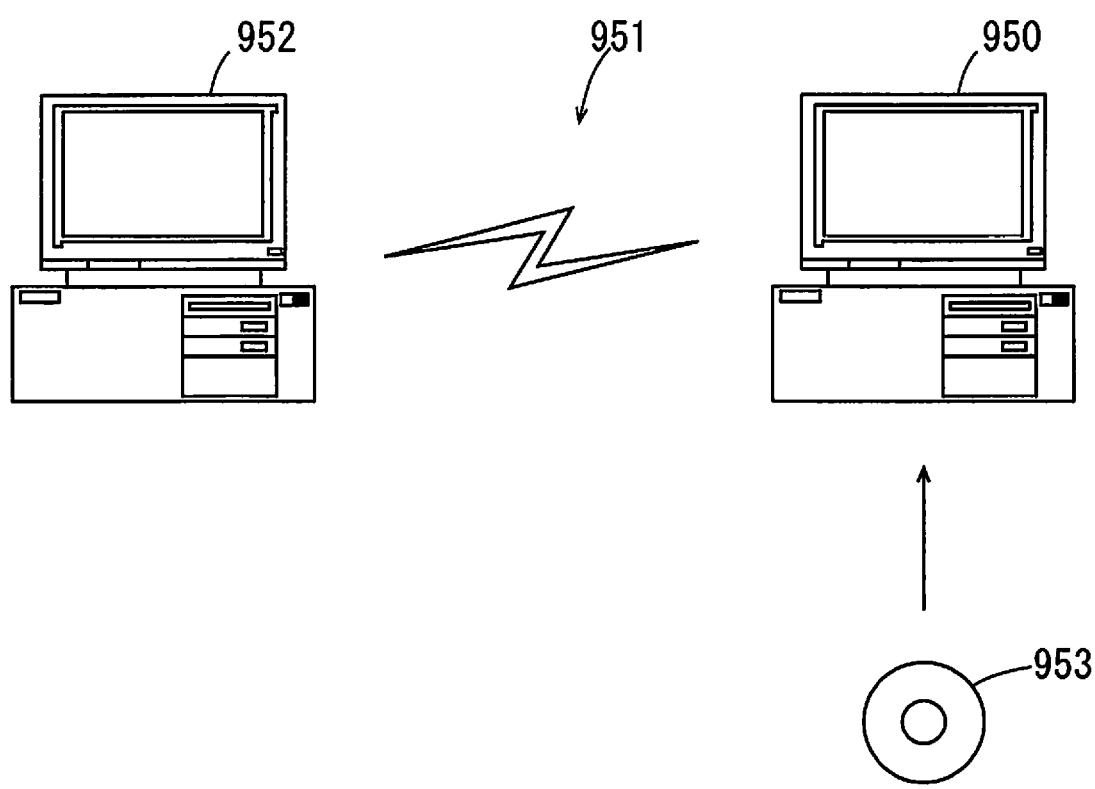
FIG. 5 is a conceptual diagram for explaining a program.

Further, in a case where being applied to a personal computer (hereinafter referred to as a PC), the program relating to the above-mentioned control can be provided via a recording medium such as a CD-ROM or a DVD-ROM, or a data signal such as the Internet. FIG. 5 is a diagram showing the appearance. A PC 950 receives a program via a CD-ROM 953. Further, the PC 950 has a function to be connected to a communication line 951. The computer 952 is a server computer that provides the above-mentioned program and stores the program in a recording medium such as a hard disc. The communication line 951 is a communication line such as the Internet or a personal computer communication, or a dedicated communication line. The computer 952 reads a program with the use of a hard disc and transmits the program to the PC 950 through the communication line 951. That is, the program is transported by a carrier wave as a data signal and transmitted through the communication line 951. In this manner, the program can be provided as a computer-readable computer program product in various forms such as a recording medium or a carrier wave.

Aspects

It is understood by those skilled in the art that the plurality of above-mentioned embodiments are specific examples of the below-mentioned aspects.

(Item 1) An analysis method according to one aspect of analyzing a second substance produced by decomposition of a first substance, includes analyzing a sample and a compound having a known concentration and detecting the first substance, the second substance and the compound, calculating an intensity or a concentration of the first substance based on data obtained by the detection and a relative response factor in regard to the first substance and the compound, and producing information about an amount or a concentration of the second substance excluding the second substance produced from the first substance in the analysis, based on an intensity or a concentration of the first substance obtained from the data. Thus, a sample that may include a subject substance and a decomposition parent substance can be analyzed more efficiently.

(Item 2) With the analysis method according to another aspect, the analysis method of the aspect described in the item 1 includes acquiring a first threshold value in regard to an intensity or a concentration of the first substance, and the analysis method produces the information based on a concentration of the second substance obtained by the data and whether an intensity or a concentration of the first substance satisfies a first condition based on the first threshold value. Thus, an effect on an amount or a concentration of a subject substance by a decomposition parent substance can be set based on a threshold value in a comprehensible manner.

(Item 3) With the analysis method according to another aspect, the analysis method described in the item 2 includes acquiring a second threshold value in regard to a concentration of the second substance, and the analysis method produces the information based on whether an intensity or a concentration of the first substance satisfies the first condition, a concentration of the second substance and the second threshold value. Thus, information about comparison between a threshold value and a concentration of a subject substance can be provided.

(Item 4) With the analysis method according to another aspect, the analysis method of the aspect described in the item 3 corrects a concentration of the second substance or the second threshold value based on whether an intensity or a concentration of the first substance satisfies the first condition, and produces the information based on whether a concentration of the second substance satisfies a second condition based on the second threshold value after the correction. Thus, an effect of a decomposition parent substance on a concentration of a subject substance can be more sufficiently reflected by correction, and information about comparison between a threshold value, and an amount or a concentration of the subject substance can be provided more correctly.

(Item 5) With the analysis method according to another aspect, the analysis method of the aspect described in any one of items 2 to 4, produces information about reliability of an analysis of the second substance based on whether an intensity or a concentration of the first substance satisfies the first condition. Thus, information about an effect of a decomposition parent substance on reliability of an analysis of a subject substance can be provided.

(Item 6) With an analysis method according to another aspect, in the analysis method of the aspect described in any of the items 1 to 4, the detection is performed by gas chromatography, liquid chromatography, mass spectrometry, gas chromatography/mass spectrometry, pyrolysis gas chromatography/mass Spectrometry, liquid chromatography/mass spectrometry, fourier transform infrared spectroscopy or spectrophotometry utilizing ultraviolet visible light. With these analysis methods, a subject substance may be produced from a decomposition parent substance. In such a case, the subject substance can be analyzed more accurately. In yet another aspect, the detection is performed by pyrolysis gas chromatography/mass spectrometry. Although a subject substance tends to be produced from a decomposition parent substance particularly in pyrolysis, the subject substance can be analyzed more accurately in such a case.

(Item 7) With the analysis method according to another aspect, in the analysis method of the aspect described in any one of items 1 to 4, the second substance is an ester of phthalic acid. It is highly important to efficiently perform a quantitative analysis on an ester of phthalic acid. Effects of the present invention are demonstrated more intensely.

(Item 8) With the analysis method according to another aspect, in the analysis method of the aspect described in the item 7, the first substance is Tris (2-ethylhexyl) trimellitate (TOTM), and the second substance is at least one compound selected from a group including Di (2-ethylhexyl) phthalate (DEHP), Di (2-ethylhexyl) trephthalate and Di (2-ethylhexyl) isophthalate. Because TOTM may produce these compounds by decomposition in an analysis, the present invention can be suitably applied.

(Item 9) With The analysis method according to another aspect, in the analysis method of the aspect described in the item 7, the first substance is tri trimellitate n-octyl (n-TOTM), and the second substance is at least one compound selected from a group including Di-n-octyl phthalate (DNOP), Di-n-octyl terephthalate and Di-n-octyl isophthalate. n-TOTM may produce these compounds by decomposition in an analysis, so that the present invention can be suitably applied.

(Item 10) With the analysis method according to another aspect, the analysis method of the aspect described in the item 8 or 9 produces information about an amount or a concentration of the second substance based on whether polyvinyl chloride is detected in an analysis of the sample, and an intensity or a concentration of the first substance. In a case where polyvinyl chloride is present, TOTM or n-TOTM is more likely to produce the above-mentioned compound due to decomposition in an analysis, so that the present invention can be suitably applied.

(Item 11) An analysis device according to one aspect is an analysis device that analyzes a second substance produced by decomposition of a first substance, and includes a measurer that detects the first substance, the second substance and a compound by an analysis of a sample and the compound having a known concentration, a calculator that calculates an intensity or a concentration of the first substance based on data obtained by the detection and a relative response factors in regard to the first substance and the compound, and an information producer that produces information about an amount or a concentration of the second substance excluding the second substance produced from the first substance in the analysis based on an intensity or a concentration of the first substance obtained from the data. Thus, a sample that may include a subject substance and a decomposition parent substance can be analyzed more efficiently.

(Item 12) A non-transitory computer readable recording medium storing a program according to one aspect is a program for causing a processing apparatus to execute a process in an analysis of a second substance produced by decomposition of a first substance, and the process includes a calculation process (corresponding to the step S1003 of the flowchart of FIG. 4) of calculating an intensity or a concentration of the first substance based on data obtained by detection of the first substance, the second substance and the compound by an analysis of a sample and a compound having a known concentration, and a relative response factor in regard to the first substance and the compound, and an information production process (corresponding to the steps S1005 to S1015) of producing information about an amount or a concentration of the second substance excluding the second substance produced from the first substance in the analysis based on an intensity or a concentration of the first substance obtained from the data. Thus, a sample that may include a subject substance and a decomposition parent substance can be more efficiently realized.

The present invention is not limited to the contents of the above-mentioned embodiment. Other aspects are possible without departing from the spirit and scope of the present invention.

Experimental Example

An experimental example in which DEHP is produced when TOTM and n-TOTM are subjected to Py-GC/MS is described below. The present invention is not limited to a condition such as a numerical value or a device of the experimental example.

<Configuration of Device>

Py-GC/MS was performed with the use of a Py-Screener system (Shimadzu Corporation). In the system, EGA/PY-3030D was used as a pyrolyzer, AS-1020E (Frontier Laboratories Ltd.) was used as an auto-shot sampler, and GCMS-QP2020 (Shimadzu Corporation) was used as a GC-MS. UA-PBDE (15 m, 0.25 mm I.D., df=0.05 μm) (Frontier Laboratories Ltd.) was used as a column.

<Creation of Calibration Curve>

Two pieces were removed by a micro puncher from 1,000 mg/kg phthalate ester resin standard sample (Shimadzu Corporation), and about 0.5 mg was analyzed by the Py-Screener. One point calibration curve was created with the use of data obtained by the analysis and used for calculation of a quantitative value of a phthalate ester.

<Analysis of Standard Sample>

In regard to TOTM, solutions (solvent:acetone) having respective concentrations of 15.3, 28.2, 39.9 mg/mL were prepared. In regard to n-TOTM, a solution (solvent:acetone) having a concentration of 39.9 mg/mL was prepared. From these solutions, samples of the below-mentioned samples of (1) and (2) were created and analyzed by the Py-Screener.

(1) Standard sample only: 5 μL of a standard solution was added to a sample cup.
(2) Standard sample+PVC: 25 mg/mL including 20 μL of a PVC solution (solvent:tetrahydrofuran; THF) and 5 μL of a standard solution was added to a sample cup.

An amount of TOTM included in a sample in which a solution having each of concentrations of 15.3, 28.3 and 39.9 mg/mL is used is equivalent to an amount of TOTM contained in 0.5 mg of sample having the TOTM concentration in resin of each of 15.3%, 28.2% and 39.9%. When a quantitative analysis of phthalate ester was performed, calculation was performed with the weight of each of these samples set to 0.5 mg.

<Result of Analysis>

A result of analysis of the standard sample of TOTM and the sample (the standard sample+PVC) to which the standard sample and the PVC solution are both added is shown in the following chart 1. In each data, n=3, and the unit is mg/kg. N.D. indicates a value smaller than 30 mg/kg. DEHP was hardly detected in the standard sample only. From 159 to 433 mg/kg of DEHP was detected in the standard sample+PVC depending on the TOTM concentration. Thus, it was found that PVC is involved with production of DEHP.

CHART 1

A result of analysis of the standard sample of TOTM and the sample to which the standard sample and the PVC solution are both added.

| SAMPLE | | STANDARD SAMPLE ONLY | STANDARD SAMPLE + PVC |
|---|---|---|---|
| CONCENTRATION OF TOTM | 15.3% | N.D. | 156 |
| | 28.2% | 31 | 259 |
| | 39.9% | 39 | 433 |

A result of analysis of the standard sample of n-TOTM and the sample (the standard sample+PVC) to which the standard sample and the PVC solution are both added is shown in the following chart 2. In each data, n=3, and the unit is mg/kg. In regard to n-TOTM, 1565 mg/kg of DNOP was detected in the standard sample only, and 1949 mg/kg of DNOP was detected in the standard sample+PVC. It was suggested that DNOP was contained in the standard sample as an impurity and an amount of DNOP increased when PVC was mixed.

CHART 2

A result of analysis of the standard sample of n-TOTM and the sample o which the standard sample and the PVC solution are both added.

| SAMPLE | | STANDARD SAMPLE ONLY | | STANDARD SAMPLE + PVC | |
|---|---|---|---|---|---|
| SUBJECT SUBSTANCE | | DEHP | DNOP | DEHP | DNOP |
| CONCENTRATION OF n-TOTM | 39.9% | 11 | 1565 | 28 | 1949 |

REFERENCE SIGNS LIST

1 . . . Analysis device, 10 . . . Pyrolysis gas chromatograph, 14 . . . Separation column, 20 . . . Pyrolysis apparatus, 30 . . . Mass spectrometry unit, 33 . . . Ionizer, 35 . . . Mass separator, 36 . . . Detector, 40 . . . Information processor, 44 . . . Outputter, 50 . . . Controller, 52 . . . Data processor, 100 . . . Measurer, 521 . . . Concentration calculator, 522 . . . Information producer, 523 . . . Determiner, 530 . . . Notifier, In . . . Ions, P1 . . . Peak corresponding to a decomposition parent substance, P2 . . . Peak corresponding to a subject substance, P20 . . . Peak corresponding to a subject substance included in a sample before an analysis

The invention claimed is:

1. An analysis method of determining a concentration of a second substance, excluding a concentration of the second substance produced from a first substance, in a sample, comprising:
analyzing the sample including a reference compound having a known concentration, the first substance, and the second substance and detecting intensity values for the first substance, the second substance, and the reference compound by an analysis device, the reference compound being stable when analyzed, and the second substance being a substance that is produced by decomposition of the first substance;

causing at least one processor to calculate a concentration of the first substance based on the intensity value of the first substance obtained by the detection and on a relative response factor in regard to the first substance and the reference compound, the relative response factor having been obtained in advance by an analysis of the first substance at a past concentration and the reference compound at the known concentration, and determine the concentration of the second substance, excluding the concentration of the second substance produced from the first substance in the analysis, based on the concentration of the first substance;

wherein the second substance is an ester of phthalic acid.

2. The analysis method according to claim 1, further comprising causing the at least one processor to acquire a first predetermined threshold value in regard to the concentration of the first substance and to compare the concentration of the first substance with the first predetermined threshold value, wherein the determining the concentration of the second substance, excluding the second substance produced from the first substance in the analysis, further comprises determining whether the concentration of the first substance satisfies a first condition based on a comparison of the concentration of the first substance with the first predetermined threshold value.

3. The analysis method according to claim 2, further comprising causing the at least one processor to acquire a second predetermined threshold value in regard to a concentration of the second substance and to compare the concentration of the second substance with the second predetermined threshold value, and wherein the determining the concentration of the second substance, excluding the second substance produced from the first substance in the analysis, further comprises determining whether the concentration of the second substance satisfies a second condition based on a comparison of the concentration of the second substance with the second predetermined threshold value.

4. The analysis method according to claim 3, further comprising causing the at least one processor to correct the concentration of the second substance if the first condition is not satisfied and to compare the concentration of the second substance with the second predetermined threshold value;

wherein the determining the concentration of the second substance, excluding the second substance produced from the first substance in the analysis, further comprises determining whether the corrected concentration of the second substance satisfies the second condition based on a comparison of the corrected concentration of the second substance with the second predetermined threshold value after the correction.

5. The analysis method according to claim 2, further comprising causing the at least one processor to output the concentration of the second substance, excluding the concentration of the second substance produced from the first substance, when the first condition is satisfied.

6. An analysis method according to claim 1, wherein the detecting intensity values of the first substance, the second substance, and the reference compound is performed by gas chromatography, liquid chromatography, mass spectrometry, gas chromatography/mass spectrometry, pyrolysis gas chromatography/mass spectrometry, liquid chromatography/mass spectrometry, Fourier transform infrared spectroscopy or spectrophotometry utilizing ultraviolet visible light.

7. The analysis method according to claim 1, wherein the first substance is Tris (2-ethylhexyl) trimellitate (TOTM), and the second substance is at least one compound selected from a group consisting of Di (2-ethylhexyl) phthalate (DEHP), Di (2-ethylhexyl) trephthalate and Di (2-ethylhexyl) isophthalate.

8. The analysis method according to claim 7, wherein the determining the concentration of the second substance, excluding the second substance produced from the first substance in the analysis, is based on whether polyvinyl chloride is detected in the analysis of the sample, and the concentration of the first substance based on the intensity value of the first substance detected by the analysis device.

9. The analysis method according to claim 1, wherein the first substance is tri trimellitate n-octyl (n-TOTM), and the second substance is at least one compound selected from a group consisting of Di-n-octyl phthalate (DNOP), Di-n-octyl terephthalate and Di-n-octyl isophthalate.

10. An analysis system that determines a concentration of a second substance, excluding a concentration of the second substance produced from a first substance, in a sample, comprising:

an analysis device configured to detect intensity values for the first substance, the second substance, and a reference compound having a known concentration by the analysis device, the reference compound being stable when analyzed, and the second substance being a substance that is produced by decomposition of the first substance;

at least one processor, wherein the at least one processor is configured to calculate a concentration of the first substance based on the intensity value of the first substance obtained by the detection and on a relative response factor in regard to the first substance and the reference compound, the relative response factor having been obtained in advance by an analysis of the first substance at a past concentration and the reference compound at the known concentration; and determine the concentration of the second substance, excluding the second substance produced from the first substance in the analysis, based on the concentration of the first substance;

wherein the second substance is an ester of phthalic acid.

11. A non-transitory computer readable recording medium storing a program for causing a computer to execute a process of determining a concentration of a second substance, excluding a concentration of the second substance produced from a first substance, in a sample, wherein the program causes the computer to execute calculating a concentration of the first substance based on detected intensities of the first substance, the second substance and a reference compound having a known concentration by an analysis device, and based on a relative response factor in regard to the first substance and the reference compound, the reference compound being stable when analyzed, and the second substance being a substance that is produced by decomposition of the first substance, and the relative response factor having been obtained in advance by an analysis of the first substance at a past concentration and the reference compound at the known concentration; and determining the concentration of the second substance, excluding the second substance produced from the first substance in the analysis, based on the concentration of the first substance;

wherein the second substance is an ester of phthalic acid.

* * * * *